(12) United States Patent
Lagunavicius et al.

(10) Patent No.: US 9,856,456 B2
(45) Date of Patent: Jan. 2, 2018

(54) DELIVERY AGENT

(71) Applicants: Arunas Lagunavicius, Vilnius (LT); Lolita Zaliauskiene, Vilnius (LT)

(72) Inventors: Arunas Lagunavicius, Vilnius (LT); Lolita Zaliauskiene, Vilnius (LT)

(73) Assignee: THERMO FISHER SCIENTIFIC BALTICS UAB, Vilnius (LT)

( * ) Notice: Subject to any disclaimer, the term of this patent is extended or adjusted under 35 U.S.C. 154(b) by 49 days.

(21) Appl. No.: 14/863,539

(22) Filed: Sep. 24, 2015

(65) Prior Publication Data

US 2016/0024475 A1 Jan. 28, 2016
US 2017/0152487 A9 Jun. 1, 2017

Related U.S. Application Data

(60) Continuation-in-part of application No. 14/147,028, filed on Jan. 3, 2014, now Pat. No. 9,481,862, which is a division of application No. 12/901,840, filed on Oct. 11, 2010, now Pat. No. 8,951,957.

(30) Foreign Application Priority Data

Oct. 12, 2009 (GB) .................................. 0917792.4

(51) Int. Cl.
C12N 5/09 (2010.01)
C08G 73/02 (2006.01)

(52) U.S. Cl.
CPC ........... *C12N 5/0693* (2013.01); *C08G 73/02* (2013.01)

(58) Field of Classification Search
None
See application file for complete search history.

(56) References Cited

U.S. PATENT DOCUMENTS

| | | | |
|---|---|---|---|
| 5,595,897 A | 1/1997 | Midoux et al. | |
| 6,013,240 A * | 1/2000 | Behr | C12N 15/88 424/1.21 |
| 6,080,724 A | 6/2000 | Chassaing et al. | |
| 6,184,037 B1 | 2/2001 | Rolland et al. | |
| 6,184,038 B1 | 2/2001 | O'Hare et al. | |
| 6,413,941 B1 | 7/2002 | Garnett et al. | |
| 6,433,017 B1 | 8/2002 | Felgner et al. | |
| 6,566,114 B1 | 5/2003 | Kauppinen et al. | |
| 6,770,479 B1 | 8/2004 | Lee et al. | |
| 6,825,341 B2 | 11/2004 | Leclerc et al. | |
| 6,841,535 B2 | 1/2005 | Divita et al. | |
| 8,173,131 B2 | 5/2012 | Tripp et al. | |
| 2001/0005717 A1 | 6/2001 | Wagner et al. | |
| 2004/0142474 A1 | 7/2004 | Mahato et al. | |
| 2004/0203154 A1 | 10/2004 | Trubetskoy et al. | |
| 2004/0248842 A1 | 12/2004 | Wagner et al. | |
| 2006/0204444 A1 | 9/2006 | Young et al. | |

FOREIGN PATENT DOCUMENTS

| | | |
|---|---|---|
| EP | 0 285 010 A2 | 10/1988 |
| EP | 0 755 924 A1 | 1/1997 |
| EP | 1 316 318 A2 | 6/2003 |
| EP | 1 316 318 A3 | 12/2003 |
| EP | 2 070 970 A2 | 6/2009 |
| GB | 2 148 266 A | 5/1985 |
| JP | 2006-233290 A | 9/2006 |
| WO | 95/24221 A1 | 9/1995 |
| WO | 96/02655 A1 | 2/1996 |
| WO | 99/36089 A1 | 7/1999 |
| WO | 01/43778 A1 | 6/2001 |
| WO | 02/42426 A2 | 5/2002 |
| WO | 03/087471 A1 | 10/2003 |
| WO | 03/095641 A1 | 11/2003 |
| WO | 2004/096998 A2 | 11/2004 |
| WO | 2005/060934 A1 | 7/2005 |
| WO | 2009/142893 A2 | 11/2009 |

OTHER PUBLICATIONS

Davison, Metabolically Inert Proteins of the Central and Peripheral Nervous System, Muscle and Tendon, Biochem J. 78 (1961) pp. 272-281.
'Inert' defined: http://dictionary.reference.com/browse/inert, published by Dictionary.com, LLC, Author unknown, no journal, no volume, no pages, retrieved Aug. 23, 2016, 1 page.
Ogris, et al. (2001) "DNA/polyethylenimine transfection particles: Influence of ligands, polymer size, and PEGylation on internalization and gene expression", AAPS PharmSci, 3(3): 43-53 (listed as pp. 1-11).
Trubetskoy. 2012. "Cationic liposomes enhance targeted delivery and expression of exogenous DNA mediated by N-terminal modified poly(L-lysine)-antibody conjugate in mouse lung endothelial cells", Biochimica et Biophysica Acta (BBA)—Gene Structure and Expression, 1131(2): 311-13 (Abstract Only).
"BioPorter Protein Delivery Reagent," http://www.genlantis.com/objects/catalog/product/extras/1077__Resource_Technical_Updates__No6.pdf Oct. 12, 2009 (two (2) sheets).
"BioTrek™ Protein Delivery Reagent Instruction Manual," Copyright 2003 http://www.stratagene.com/manuals/204140.pdf (seven (7) sheets).
"Penetratin™ 1 Peptide," Krackeler Scientific, Inc. http://www.krackeler.com/products/fid/2819 Sep. 29, 2009 (two (2) sheets).
"Pep-1 (Uncapped)," Genscript, http://www.genscript.com/peptide/RP10130-Pep-1_peptide.html. Accessed: Sep. 29, 2009 (two (2) sheets).
"Profect Protein Delivery Reagents Product Applications Guide 2008," http://www.targetingsystems.net/profect.pdf. Oct. 12, 2009 (six (6) sheets).
"Pro-Ject Protein transfection reagent," Thermo Scientific., http://www.piercenet.com/Objects/View.cfm?type=productFamily&ID=A21BD675-A083-4D56-A6BO-F1F6BA6DA446. Accessed: Sep. 18, 2009 (two (2) sheets).
"ProteoJuice™ Protein Transfection Reagent," Merck http://www.merckbiosciences.co.uk/Products/ProductDisplay.asp?catno=71281. Sep. 29, 2009 (two (2) sheets).
"ProVectin™ Protein Delivery Reagent." Imegenex.http://www.imgenex.com/provectin.php. Accessed: Sep. 18, 2009 (one (1) sheet).

(Continued)

*Primary Examiner* — Robert M Kelly
(74) *Attorney, Agent, or Firm* — Thompson Hine LLP

(57) ABSTRACT

A composition comprising a polycationic agent and a polyanionic agent, and kits comprising the composition, is provided. In embodiments, the polyanionic agent is a nucleic acid and the polycationic agent is a modified polyalkyleneimine polymer.

9 Claims, 10 Drawing Sheets

(56) References Cited

OTHER PUBLICATIONS

"PULSin™ Delivery Reagent of Functional Proteins/Antibodies and Peptides to Living Cells," http://www.polyplus-transfection.com/EN/produit.php?PAGEID=131. Accessed: Sep. 18, 2009 (three (3) sheets).
"TransPass™ P Protein Transfection Reagent," New England BioLabs Inc., http://www.neb.com/nebecomm/products/productM2563.asp, Accessed: Sep. 29, 2009 (two (2) sheets).
"TransVector™," Krackeler Scientific, Inc., http://www.krackeler.com/products/fid/2820 Accessed: Sep. 29, 2009 (one (1) sheet).
"Voyager™ NES Protein Production Kits," Invitrogen. http://tools.invitrogen.com/content/sfs/manuals/voyagernesprotprodkits_man.pdf. Apr. 7, 2004 (two (2) sheets.
Antoine Kichler, "Gene Transfer with modified polyethylenimines", The Journal of Gene Medicine, Review Article, 2004, pp. S3-S10, vol. 6.
Baranauskas, Aurimas, "Biochemical Properties of methyl-specific restriction endonuclease," Biochemistry Masters Thesis, Vilnius University (2006). Abstract only. (three (3) sheets).
Bragonzi, A. et al., "Comparison between cationic polymers and lipids in mediating systemic gene delivery to the lungs", Gene Therapy, (1999), vol. 6, pp. 1995-2004.
British Search Report dated Apr. 14, 2008 (Four (4) pages).
Brown, M. D. et al., "Gene delivery with synthetic (non-viral) carriers," International Journal of Pharmaceutics, (2001), vol. 229, pp. 1-21.
Chariot™ Simple, efficient protein delivery, http://www.activemotif.com/documents/5.pdf. Oct. 12, 2009, (six (6) sheets).
De Smedt, S. C. et al., "Cationic Polymer Based Gene Delivery Systems", Pharmaceutical Research, (2000), vol. 17, No. (2), pp. 113-126.
European Search Report dated Mar. 9, 2010 (Three (3) pages).
Ferrari, S. et al. "ExGen 500 is an efficient vector for gene delivery to lung epithelial cells in vitro and in vivo", Gene Therapy, (1997), vol. 4, pp. 1100-1106.
Florea, B. I. et al., "Transfection Efficiency and Toxicity of Polyethyleneimine in Differentiated Calu-3 and Nondifferentiated Cos-1 Cell Cultures", The AAPS PharmSci, (2002), vol. 4, No. (3), article 12, pp. 1-11.
Forrest, M. L. et al., "A Degradable Polyethylenimine Derivative with Low Toxicity for Highly Efficient Gene Delivery", Bioconjugate Chem., (2003), vol. 14, pp. 934-940.
Francoise Leclercq et al., "Synthesis of Glycosylated Polyethyleneimine with Reduced Toxicity and High Transfecting Efficiency", Bioorganic & Medicinal Chemistry Letters, 2000, pp. 1233-1235, vol. 10.
Futami et al., "Intracellular delivery of proteins into mammalian living cells by polyethylenimine cationization", Journal of Bioscience and Bioengineering, vol. 99, No. 2, pp. 95-103, Feb. 2005 (twelve (12) sheets).
Gao, X. et al., "Nonviral Gene Delivery: What We Know and What is Next", The AAPS Journal, (2007), vol. 9, No. (1), article 9, pp. E92-E104.
Gosselin, M. A. et al., "Efficient Gene Transfer Using Reversibly Cross-Linked Low Molecular Weight Polyethylenimine", Bioconjugate Chem., (2001), vol. 12, pp. 989-994.
Great Britain Search Report on GB0917792.4, dated Feb. 11, 2010 (four (4) sheets).
Harlow, Jay, "Sea Scallops: How to Avoid Getting Soaked," Sally's Place, http://www.sallybernstein.com/food/columns/harlow/sea-scallops.htm (2002) Accessed: Nov. 19, 2012 (three (3) sheets).
International Search Report and Written Opinion, PCT/EP2010/065236, dated Mar. 29, 2011 (nine (9) sheets).
Klimasauskas, Saulius, "New enzymes and technologies epigenetics analysis," Project EPIGEN, Biotechnologijos Institutes, Registration No. P-07003, Contract No. P—Mar. 2008 (2008). Abstract only. (three (3) sheets).
Li et al. (May 1, 2006) "Synthesis of lipopolyhydroxy-alkyleneamines for gene delivery," Bioorganic & Medicinal Chemistry Letters, 16(9), 2428-2432.
DeliverX™ Peptide Transfection Kit. Panomics. Copyright 2006 (two (2) sheets).
DeliverX™ Peptide Transfection Accessed: Sep. 29, 2009 Kits. Panomics. http://www.panomics.com/product/43/. Copyright 2009. Accessed: Sep. 29, 2009 (two (2) sheets).
Patil, S. D. et al., "DNA-based Therapeutics and DNA delivery systems: A Comprehensive Review", The AAPS Journal, (2005), vol. 7, No. (1), article 9, pp. E61-E77.
Protein transfection reagent SAINT-PhD. Synvolux Therapeutics. http://www.synvolux.com/protein-transfection-reagent-saint-phd.html. Accessed: Jul. 2, 2011 (one (1) sheet).
Roberts, Josh, "Buyers Guide to Protein Transduction Reagents—A range of chemicals and peptides are available to help get proteins into cells," The Scientist (Jun. 7, 2004) vol. 18 Pt. 11, pp. 42 and 43 (Three (3) sheets).
Shigeta et al., "Anti-RNA Virus Activity of Polyoxometalates," Biomedicine & Pharmacotherapy, vol. 60, No. 5, pp. 211-219, available online May 24, 2006 (nine (9) sheets).
Zaliauskiene et al., Efficient Gene Transfection Using Novel Cationic Polymers Poly(hydroxyalkylene imines). Bioconjugate Chemistry 21 (2010) 1602-1611.

\* cited by examiner

Figure 1. Polyanions improve polycation-mediated antibody delivery into HeLa cells.

Figure 2. Polycationic polymer pHP transduced β-galactosidase is primarily detected in the cytoplasmic fraction.

Figure 3. Different polyanions enhance cationic polymer pHP mediated protein transfection Figure 4. Polyanions enhance different polycation (pHP and LPEI) mediated protein transfection efficiency.

Figure 5a. Polyanion NaPWp enhances pHP-mediated peptide and inert protein (BSA) transfections.

Figure 5b. Polyanion NaPWp enhances different pI having protein transduction.

Figure 6. Polyanion (pWP) enhances pHP mediated protein transfection into primary and suspension cells.

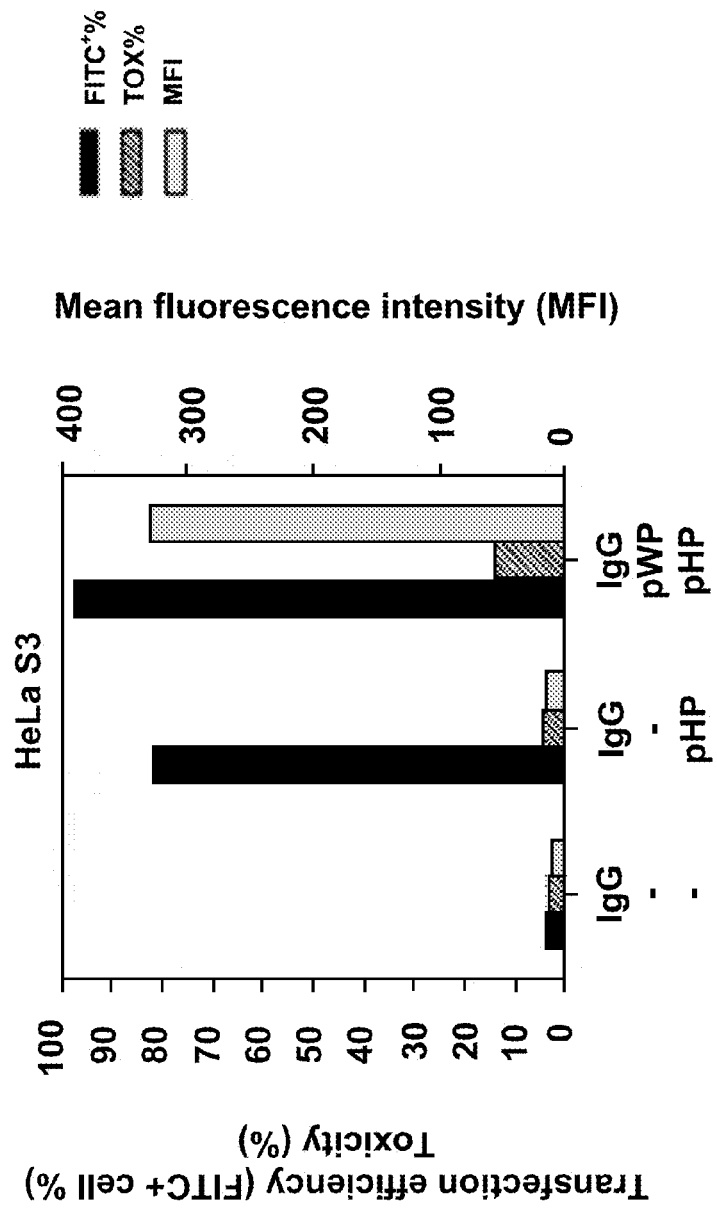
Figure 6. Polyanion (pWP) enhances pHP mediated protein transfection into primary and suspension cells.
Fig. 6 (con't)

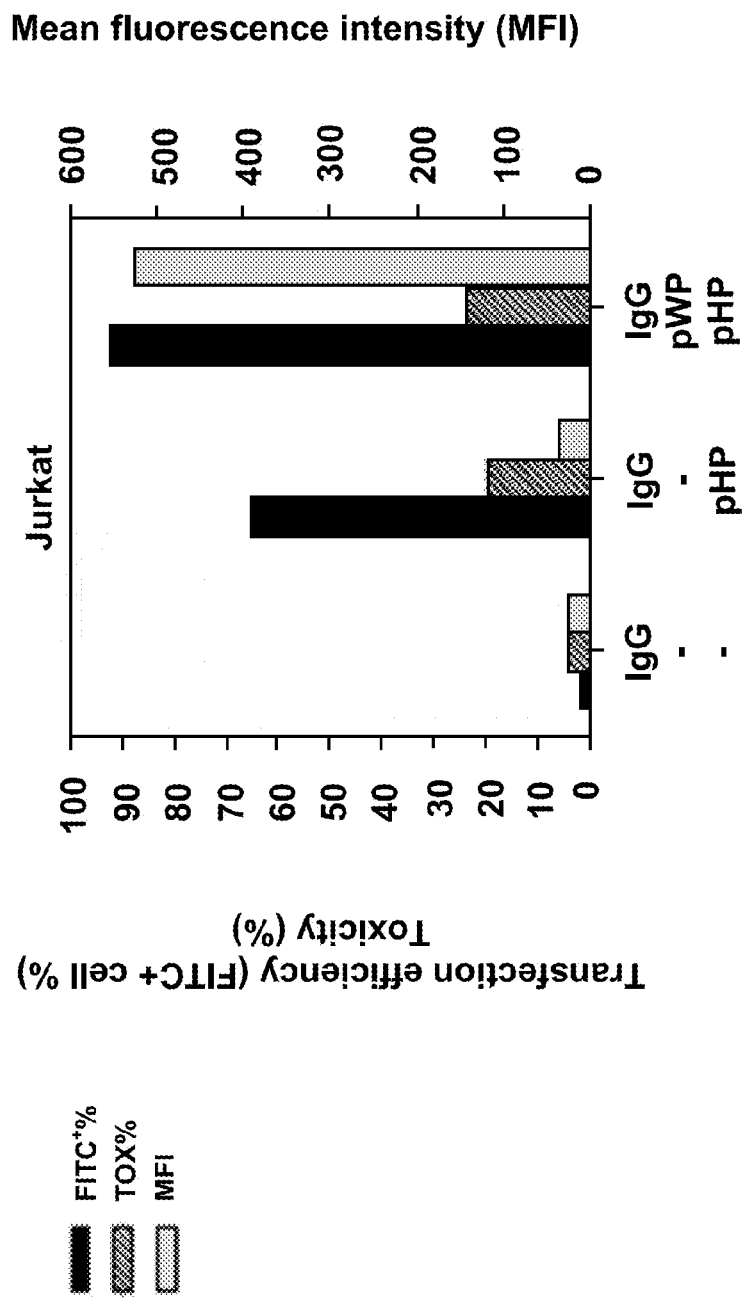
Figure 6. Polyanion (pWP) enhances pHP mediated protein transfection into primary and suspension cells.
Fig. 6 (con't)

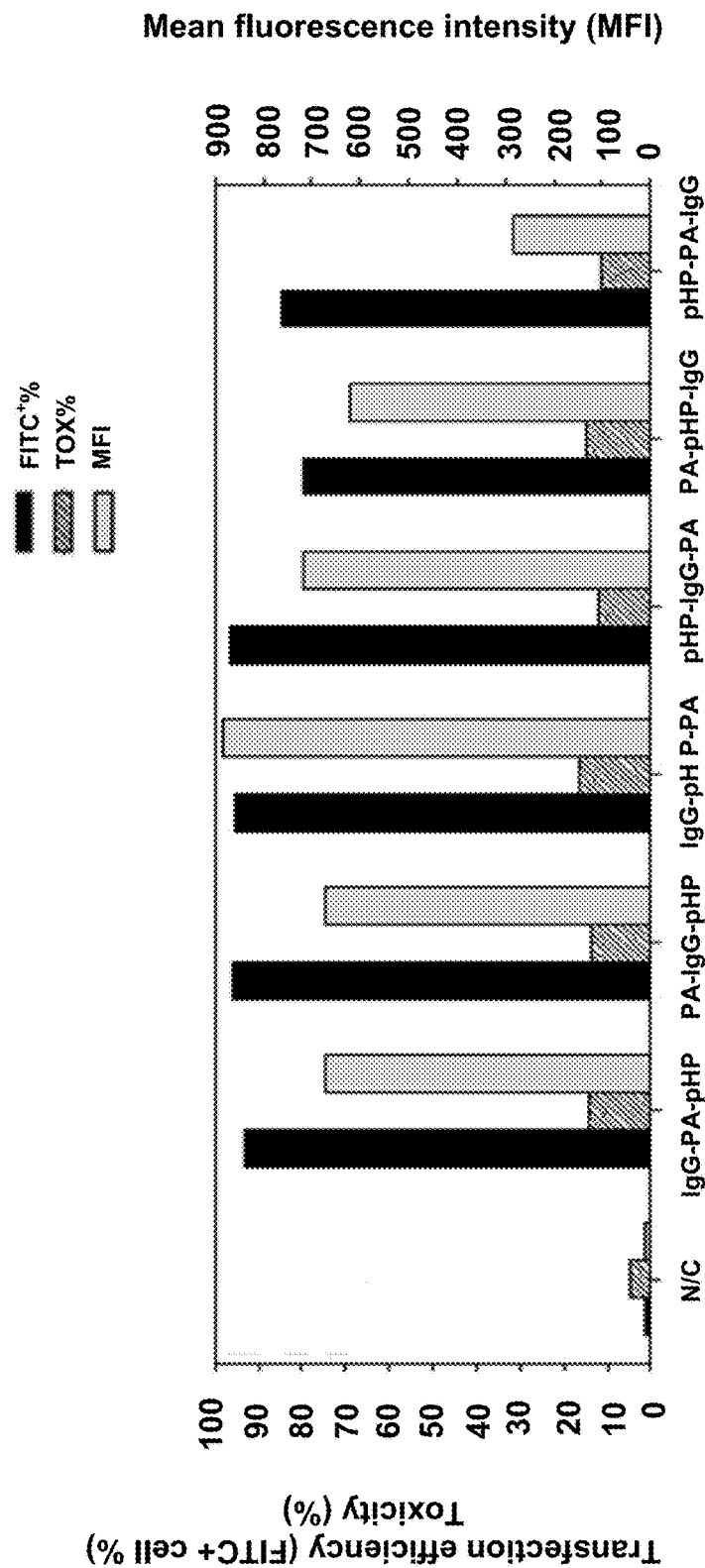
Figure 7. Component mixing order has little effect on protein transfection efficiency.

DELIVERY AGENT

RELATED APPLICATIONS

This application is a Continuation-in-Part of U.S. application Ser. No. 14/147,028 filed Jan. 3, 2014 now U.S. Pat. No. 9,481,862; which is a divisional of U.S. application Ser. No. 12/901,840 filed Oct. 11, 2010 which issued as U.S. Pat. No. 8,951,957; which claims priority to Great Britain application Serial No. 0917792.4 filed Oct. 12, 2009, each of which is expressly incorporated by reference herein in its entirety.

FIELD OF INVENTION

The present invention relates to a composition for delivering a peptide or protein into a cell, a kit for delivering a peptide or protein into a cell and a method therefor, as well as uses of the compositions and kits.

BACKGROUND OF INVENTION

Abbreviations

P/P—peptide or protein
PA—polyanionic agent
pHP—polyhydroxypropyleneimine
pWP—sodium phosphotungstate tribasic hydrate ($Na_3O_{40}PW_{12}.xH_2O$);
pW—sodium polytungstate ($Na_6O_{39}W_{12}.H_2O$);
pMoP—sodium phosphomolybdate hydrate ($Mo_{12}Na_3O_{40}P.xH_2O$);
pMo—ammonium molybdate tetrahydrate ($H_{24}Mo_7N_6O_{24}.4H_2O$);
pP—sodium polyphosphate $(NaPO_3)_{12-13}xNa_2O$ Efficient foreign protein delivery into living cells can completely bypass transcription-translation processes related to gene expression, reducing the time required for target protein synthesis from days to hours.

The ideal peptide/protein (P/P) delivery method/agent into eukaryotic cells should meet three major criteria: i) it should efficiently bring P/P into the cells; ii) it should protect P/P against denaturation and degradation; iii) the method itself should be non-toxic to the host cells.

In general, P/P delivery or transfection techniques include physical delivery methods, such as microinjection, electroporation, and methods based on chemical transfection agents of different origin that facilitate protein delivery into the cell. A general characteristic of a protein delivery agent is its ability to form positively charged complexes with target P/P, which are capable of attaching themselves to negatively charged cell surfaces, crossing through the plasma membrane and delivering the captured protein into the cell. Usually the transfection agent stabilizes the protein, protects it from degradation and preserves its natural characteristics during transfection.

The most popular commercially available current protein delivery agents are presented in Table 1.

TABLE 1

| Peptide/protein (P/P) delivery into cells. | | | |
|---|---|---|---|
| Company | Product | Characteristics | Method/agent reference |
| Active Motif | Chariot | P/P forms non-covalent complex with Chariot peptide | U.S. Pat. No. 6,841,535 |
| GenScript Corp. | Pep-1 | P/P forms non-covalent complex with Pep-1 peptide | U.S. Pat. No. 6,841,535 |
| Invitrogen | Voyager | Voyager products are bacterial and mammalian expression systems for the production of polypeptides fused with VP22. | U.S. Pat. No. 6,184,038 |
| Krackeler Scientific Inc./ Qbiogene | TransVector | TransVector is a bacterial expression system for the production of purified polypeptides fused with Penetratin. | U.S. Pat. No. 6,080,724 |
| Krackeler Scientific Inc./ Qbiogene | Penetratin 1 peptide | Penetratin 1 peptide is activated peptide for chemical conjugation with target P/P. | U.S. Pat. No. 6,080,724 |
| Panomics | DeliverX | P/P forms non-covalent nanoparticles with virus-derived amphipathic peptides (MPG peptide technology) | U.S. Pat. No. 6,841,535 |
| Imgenex | ProVectin | Encapsulation of P/P in liposomes or association of P/P with liposomal membrane. | |
| Genlantis/ Gene Therapy Systems | BioPorter | P/P forms non-covalent complexes with cationic lipids mixture. | WO03095641A1 |
| Pierce | Pro-Ject | P/P forms non-covalent complexes with cationic lipids mixture. | |
| Stratagene | BioTrek | P/P forms non-covalent complexes with lipid formulated reagent. | |

TABLE 1-continued

Peptide/protein (P/P) delivery into cells.

| Company | Product | Characteristics | Method/agent reference |
|---|---|---|---|
| Synvolux Therapeutics | SAINT PhD | P/P forms non-covalent complexes with cationic pyridinium amphiphile and a helper lipid. | EP0755924B1 |
| Targeting Systems | ProFect-P1, ProFect-P2 | P/P forms non-covalent complexes with: i) lipid reagent (ProFect-P1); ii) with non-lipid reagent (ProFect-P2). | |
| NEB | TransPass P | P/P forms non-covalent complexes with non-lipid polimer. | |
| Novagen | ProteoJuice | P/P forms non-covalent complexes with reagent, which differs substantially from protein delivery systems based on lipids or protein transduction domains. | |
| Polyplus transfections | PULsin | P/P forms non-covalent complexes with cationic amphiphile molecule. | |

Based on the origin of material, P/P transfection agents can be classified into three major groups: i) cationic peptides; ii) cationic lipids; iii) other cationic reagents/polymers (e.g. polyamines). As an alternative, transfection agents can be covalently bound to target peptide/protein: by i) genetic fusion (e.g. cationic peptides); ii) by chemical conjugation. There are many known peptide/protein delivery methods that have been successfully commercialized, however, all of them have certain limitations in their application or efficacy regarding the type of target protein, its pI or molecular weight or the types of cells used for transfection. Therefore, there is a need in the market for efficient, universal and robust protein delivery agents.

SUMMARY OF THE INVENTION

In a first aspect, the present invention provides a composition for delivering a peptide or protein into a cell, which composition comprises a polycationic agent and a polyanionic agent, wherein the polyanionic agent comprises an inorganic polyphosphate or a polyoxometalate.

There is further provided a kit for delivering a peptide or protein into a cell, which kit comprises a polycationic agent in a first container and a polyanionic agent in a second container, wherein the polyanionic agent comprises an inorganic polyphosphate or a polyoxometalate.

In a further aspect, the present invention provides use of a composition for delivering a peptide or protein into a target cell, which composition comprises a polycationic agent and a polyanionic agent, wherein:
(1) the polyanionic agent comprises a polyphosphate or a polyoxometalate; and/or
(2) the polycationic agent comprises a polyalkyleneimine.

There is further provided use of a kit for delivering a peptide or protein into a target cell, which kit comprises a polycationic agent in a first container and a polyanionic agent in a second container, wherein;
(1) the polyanionic agent comprises a polyphosphate or a polyoxometalate; and/or
(2) the polycationic agent comprises a polyalkyleneimine.

It has surprisingly been found that a composition comprising a polycationic agent and a polyanionic agent in which the polyanionic agent comprises a polyphosphate or a polyoxometalate has improved properties for delivering a peptide or protein into a cell. Peptide or protein delivery according to the invention is characterised by a more efficient, uniform and robust performance over a wide range of peptides and proteins of interest, including those of different pI and those of different molecular mass. When compared with prior art methods, it was found that transfection efficiency according to the invention was increased.

Without wishing to be bound by theory, it is thought that positively charged cationic agents alone are capable of interacting efficiently with negatively charged peptides or proteins. They are thought to be condensed into nano-sized complexes termed polyplexes which deliver encased peptide or protein material into the cell. Whilst such transfection reagents as in the prior art may be capable of delivering negatively charged biomolecules such as nucleic acids and proteins, different proteins have neutral, negative or positive charges and therefore are not thought to interact with the cationic agents with the same efficiency. According to the invention, by adding a polyanionic agent, its interaction with the peptide or protein of interest may assist in overcoming this problem and ensure that the polyanionic agent coated protein will have a negative charge. This enables it to interact efficiently with the polycationic agent and subsequently be transported through the cell membrane. This is thought to give rise to delivery agents which are more efficient, and which offer a more uniform and robust performance over a wide range of peptides or proteins of interest rather than just some.

Typically, the polyanionic and polycationic agents of the invention interact with each other ionically. They may also interact ionically with the peptide or protein of interest. This is an advantageous property because there is no need, for example, for the polyanionic agent to have a functional group for covalent coupling to the peptide or protein. Likewise, there is no need for the polycationic agent to have such a functional group. Accordingly, the composition does not need to incorporate an agent for covalent coupling to the peptide or protein. Advantageously, no agent for covalent coupling is present in the composition.

The polycationic agent of the invention may be lipidic, for example comprising a plurality of cationic lipids which may be organised in a supramolecular structure such as a liposome. A polycationic agent which comprises a cationic polymer is preferred. Such cationic polymers may be polylysine or polyarginine, Particularly suitable cationic polymers include polyalkyleneimine polymers such as polyethyleneimines (such as described in U.S. Pat. No. 6,013,240) or polyhydroxyalkyleneimines. Cationic polyalkyleneimine polymers having a repeat unit comprising a hydrophilic group are described herein in which the hydrophilic group is in the polymer backbone or pendant from the polymer backbone and wherein the hydrophilic group preferably comprises a heteroatom. Polyhydroxyalkyleneimine polymers are preferred, such as poly(2-hydroxy)propyleneimine.

A cationic polyalkyleneimine polymer having a repeat unit comprising a hydrophilic group is provided. In one embodiment, the hydrophilic group is in the polymer backbone. In one embodiment, the hydrophilic group is pendant from the polymer backbone. In one embodiment, preferably, there are as many imine groups as hydrophilic groups. (i.e. a 1:1 ratio). In another embodiment, preferably the ratio of imine groups:hydrophilic groups is 2:1. Typically, the hydrophilic group, referred to elsewhere herein as X1 or X2, comprises a heteroatom. The cationic polyalkyleneimine polymer according to the invention may be linear or branched. According to the present invention, the term "branched" means branching of the polyalkyleneimine polymer per se. "Branched polyalkyleneimine polymer" does not mean a polyalkyleneimine polymer having a second, different polymer grafted thereto.

Preferably, in the polymer having a repeat unit comprising a hydrophilic group, said repeat unit has a structure as shown in formula V, more preferably formula I:

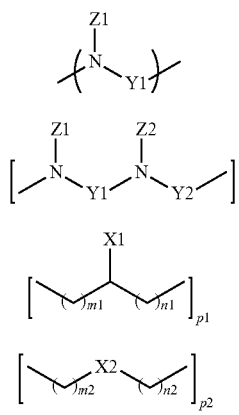

where:
Y1 and Y2 each independently represent a group having formula II or III;
Z1 and Z2 each independently represent —H, alkyl or a branching chain;
X1 represents —H, -alkyl, or a hydrophilic group, X2 represents —CH2-, —CH(alkyl), —C(alkyl)2- or hydrophilic group, provided that at least one of X1 and X2 is a hydrophilic group;
m1, m2, n1 and n2 each independently is 0, 1, 2 or 3; and
p1 and p2 each independently is 1 or 2.

When Z1 and/or Z2 are branching chains it will be understood that Z1 and/or Z2 each represent another cationic alkyleneimine polymer chain having a repeat unit comprising a hydrophilic group. In this way, the cationic alkyleneimine polymer will be branched. Preferred alkyl Z1 and Z2 groups include
—CH3, and —C2H5. Other repeat units may be present in the polymer.

When Z1=Z2 and Y1=Y2, the cationic alkyleneimine polymer can be a homopolymer of a repeat unit having a structure as shown in formula IV:

where Z=Z1=Z2 and Y=Y1=Y2. The polymer could be further defined as a homopolymer of AA (formula VII) type or BB (formula VIII) type.

When Z1≠Z2 and/or Y1≠Y2, the cationic alkyleneimine polymer can be a copolymer of a first repeat unit having a structure as shown in formula V and a second, different repeat unit having a structure as shown in formula VI:

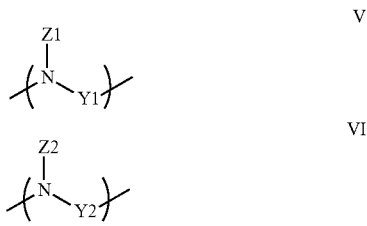

Such polymers could be defined as a copolymer of AA* (formula IX) and BB* (formula X) types. The cationic alkyleneimine polymer may be a regular alternating AB copolymer (formula XI), though a random AB copolymer may be considered also in one embodiment.

Preferred cationic alkyleneimine polymers according to the invention have a repeat unit selected from one of formulae VII to XI:

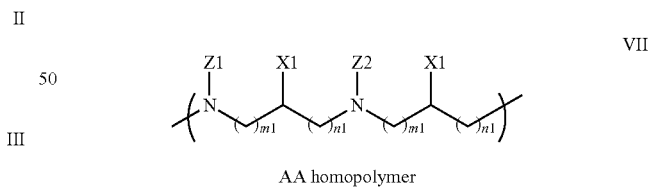

AA homopolymer where Z1=Z2 and, with reference to general formula I, Y1=Y2=a group having formula II.

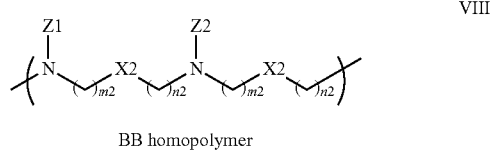

BB homopolymer where Z1=Z2 and, with reference to general formula I, Y1=Y2=a group having formula III.

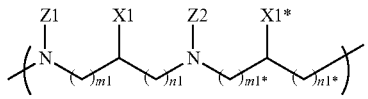

AA* copolymer where Z1 is the same as or different from Z2. In other words, with reference to general formula I, Y1≠Y2 and Y1 and Y2 each independently represent a group having general formula II.

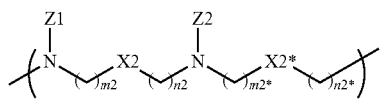

BB* copolymer where Z1 is the same as or different from Z2. In other words, with reference to general formula I, Y1≠Y2 and Y1 and Y2 each independently represent a group having general formula III.

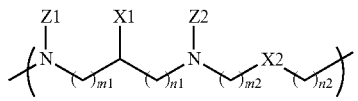

AB copolymer where Z1 is the same as or different from Z2. In other words, with reference to general formula I, Y1≠Y2 and Y1 represents a group having formula II and Y2 represents a group having formula III.

Throughout this specification, the use of "*" means that X1* can be different from X1, X2* can be different from X2, m1* can be different from m1, n1* can be different from n1, m2* can be different from m2, and n2* can be different from n2.

X1 and X1* independently are selected from —H, alkyl, or a hydrophilic group, provided that in formula IX at least one of X1 and X1* represents a hydrophilic group.

Preferably, X1 and X1* independently are selected from the group consisting of —H, alkyl, —OH, —SH, —NH₂, —N(alkyl)₂, —NH(alkyl), —CONH₂, —NHCONH₂, —CN

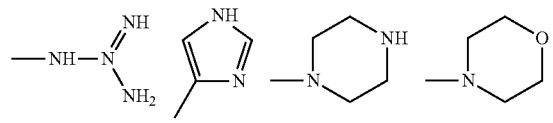

provided that in formula IX at least one of X1 and X1* represents a hydrophilic group (i.e. not H or alkyl in the list above).

X2 and X2* independently are selected from the group consisting of —CH₂—, —CH(alkyl)-, C(alkyl)₂- and a hydrophilic group provided that in formula X at least one of X2 and X2* represents a hydrophilic group.

Preferably, X2 and X2* independently are selected from the group consisting of —CH₂—, —O—, —S—, —NH—, —N(alkyl)-, provided that in formula X at least one of X2 and X2* represents a hydrophilic group (i.e. not —CH₂— in the list above).

A preferred polymer according to the invention is poly (2-hydroxypropyleneimine) (pHP), i.e. a homopolymer having an AA a repeat unit of formula XII:

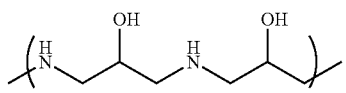

Other preferred polymers according to the invention include poly (2-hydroxypropyleneimine ethyleneimine) (pHPE) and poly (2-hydroxypropyleneimine propyleneimine) (pHPP), i.e. AB copolymers having an AB repeating unit of formula XIII or XIV:

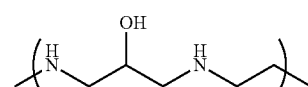

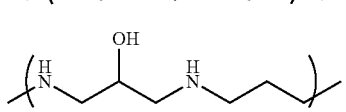

The degree of polymerisation (d) of polymers having a repeat unit as shown in any one of general formulae I, or VII to XIV preferably is >1, more preferably in the range from 1 to 1000, more preferably from 30 to 500. Accordingly, a polymer according to the invention may have the formula:

$$\text{--(repeat unit of general formula I)}_d$$

The molecular weight of the cationic polyalkyleneimine polymer according to the first aspect preferably is in the range of from 1 to 100 kDa, more preferably 5 to 30 kDa. Molecular weight can be measured by size exclusion chromatography (SEC). For a linear polymer, the molecular weight will provide a direct indication of chain length i.e. the degree of polymerisation. However, SEC provides scarce information on polymer branching.

A cationic polyalkyleneimine polymer of the invention may be obtained by any suitable method.

A second aspect of the present invention provides a method of making a modified polyalkyleneimine polymer as defined by a polycondensation reaction.

A preferred polycondensation reaction is between first monomers each having two reactive groups and second monomers each having two reactive groups, said reactive groups being selected from —Cl, —Br and —I, tosyl, mesyl —NH₂ and NHR. A preferred polycondensation reaction is between first monomers each having two reactive groups selected from —NH₂ or NH (alkyl) and second monomers each having two halide reactive groups, selected from —Cl, —Br, —I, tosyl and mesyl.

A -tosyl or mesyl group may be used in place of a halide reactive group.

Random copolymers can be obtained by using more than two different monomers in the polymer feed. For example, using three monomers Hal-A-Hal, NH₂-A-NH₂, and NH₂—B—NH₂ in the polymer feed for the polycondensation reaction will produce random AB type copolymers. Higher order polymers two also may be made. For example, using 3 monomers Hal-A-Hal, NH₂—B—NH₂, Hal-C-Hal in the polymer feed for the polycondensation reaction will produce random ABC type copolymers.

It will be appreciated that repeat units as illustrated throughout this application may be derived from a single monomer carrying suitable reactive groups. Similarly, repeat units as illustrated throughout this application may be derived from two or more monomers, each carrying suitable reactive groups.

The two reactive groups on a single monomer could be the same or different from one another. However, for ease of processing they will generally be the same.

In one embodiment, the halide reactive groups are both Br.

In one embodiment, the first monomer has formula XV:

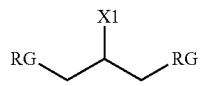

XV where RG represents a reactive group as defined anywhere herein and X1 represent a hydrophilic group as described anywhere herein.

Preferably, X1 represents OH.

A single monomer may have only two or more than two reactive groups selected from the reactive groups defined above.

Preferably, the ratio of first monomer:second monomer in the polymer feed is in the range 52:48 to 48:52, more preferably about 50:50.

The molecular weight distribution of the modified polyalkyleneimine polymer produced according to the method of the second aspect preferably is in the range of from 1 to 100 kDa, more preferably 5 to 30 kDa. Molecular weight distribution can be measured by size exclusion chromatography.

One general reaction scheme for a polycondensation reaction is shown below:

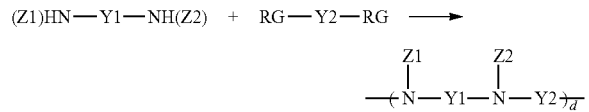

where d is the degree of polymerisation; RG represents a reactive group selected from —Cl, Br, —I, -tosyl and -mesyl; and Z1, Y1 and Y2 are as defined anywhere herein.

The product of the method according to the second aspect may be linear polymers, branched polymers or a mixture of linear and branched polymers.

During the polycondensation reaction, some branching may occur. Branching occurs by the replacement of H by another covalently bonded chain of that polymer.

Suitable solvents in which to carry out the polycondensation reaction will be known to a person skilled in this art and include methanol or a mixture of methanol and water.

A suitable temperature at which to carry out the polycondensation reaction will be known to a person skilled in this art. A suggested temperature is about 10° C. lower than the reflux temperature of the reaction mixture, preferably about 50° C.

The polymer product of the polycondensation reaction may be purified by one or more suitable purification techniques, for example by visking dialysis, as is known in the art.

The purified polymer product may be concentrated by one or more suitable techniques, for example by freeze drying, as is known in the art.

The polyanionic agent is preferably an anionic polymer, which may be an organic or inorganic polymer. In one arrangement the anionic polymer comprises a polyphosphate, which may be a heterophosphate or a homophosphate. The heterophosphate may comprise a nucleic acid in the form of an oligo or polynucleotide such as DNA or a synthetic analogue thereof, GNA, TNA and LNA being typical examples. It is preferred that the polycationic agent is not lipidic, especially where a nucleic acid is used as the polyanionic agent according to the invention.

Where the polyphosphate comprises a homophosphate, this may be an inorganic phosphate such as sodium polyphosphate $(NaPO_3)_x$.

Alternatively, the anionic polymer may comprise a polyoxometalate. Polyoxometalates are polyatomic ions, usually anions, which comprise three or more transition metal oxyanions linked together with shared oxygen atoms to form large, closed 3-dimensional frameworks. The metal atoms that make up the frameworks are sometimes called addenda atoms and the framework may comprise one or more different addenda atoms. These addenda atoms are typically group 5 or group 6 transition metals and may be present in the framework in high oxidation states. Examples of the transition metal atoms include molybdenum and tungsten. The framework of the polyoxometalates may optionally incorporate one or more heteroatoms such as phosphorus. As discussed in further detail below, ammonium molybdate tetrahydrate, sodium phosphotungstate tribasic hydrate and sodium phosphomolybdate hydrate are all useful in the present invention, especially sodium polytungstate.

Compositions according to the invention may be used to deliver a wide range of peptides or proteins as discussed herein. Such peptides or proteins include enzymes such as β-galactosidase, antibodies and inert proteins such as bovine serum albumin. It is possible according to the invention to deliver polypeptides of different pIs and different molecular masses, as discussed further in the examples set out below.

The invention may be used to deliver peptides or proteins to a variety of cells, including cells in suspension, adherent cells and primary cells. The invention may be used to deliver to cells in vitro or in vivo.

Kits according to the invention may be supplied with additional containers containing suitable buffers or other reagents for use with the polyanionic and polycationic agents according to the invention. Instructions for use of the kit may also be supplied therewith.

In a further aspect the present invention provides a method for delivering a peptide or protein into a target cell, which method comprises contacting the peptide or protein with a polycationic agent and a polyanionic agent to form a complex and contacting the complex with the target cell so as to deliver the peptide or protein thereto, wherein;

(1) the polyanionic agent comprises a polyphosphate or a polyoxometalate; and/or (2) the polycationic agent comprises a polyalkyleneimine.

According to the method of the invention, it is possible to contact the polyanionic agent with the polycationic agent and with the peptide or protein in any order. In a preferred embodiment, the polyanionic agent is contacted with the peptide or protein prior to contact with the polycationic agent. It is thought that the peptide or protein may form a complex with the polyanionic agent and this complex then interacts with the polycationic agent to form a delivery complex. Complexes according to the invention are advantageously formed by ionic interactions.

According to the invention it is possible to deliver the peptides or proteins to cells in vitro, for example in a molecular biology application such as in the study of the role of a protein in the regulation of different cellular processes.

In a further aspect the compositions of the invention may be used for therapeutic or diagnostic applications as for example in the manufacture of a medicament. According to this aspect, for example, a therapeutic protein or peptide may be delivered to a subject in vivo.

Thus, there is further provided use of a composition for the manufacture of a medicament for delivering a peptide or protein into a cell, which composition comprises a polycationic agent and a polyanionic agent, wherein;
(1) the polyanionic agent comprises a polyphosphate or a polyoxometalate; and/or
(2) the polycationic agent comprises a polyalkyleneimine.

In this way, the medicament acts a vehicle for delivering the therapeutic peptide or protein and would need to be prepared to a level of purity and stability suitable for administration to a subject.

There is further provided a product comprising a peptide or protein, a polycationic agent, and a polyanionic agent as a combined preparation for use in medicine, wherein;
(1) the polyanionic agent comprises a polyphosphate or a polyoxometalate; and/or
(2) the polycationic agent comprises a polyalkyleneimine.

In this further aspect, the combined preparation of the invention typically comprises either a kit for delivering a therapeutic peptide or therapeutic protein in which the peptide or protein, polyanionic agent and polycationic agent are stored in separate containers; or a unitary composition in which each component is present so as to form a complex for administration to the subject.

The invention will now be described in further detail, by way of example only, with reference to the accompanying drawings in which:

FIG. 7 shows the effect of component mixing on protein transfection as measured by transfection efficiency, toxicity and mean fluorescence intensity.

DETAILED DESCRIPTION OF THE INVENTION

Transfection efficiency of Polyhydroxypropyleneimine (pHP) was initially tested on HeLa cells using Alexa Fluor (AF) 488-labeled antibody (goat IgG) as a control protein. Different polyanions: DNA, sodium polyphosphate (pP) and sodium polytungstate (pW) were tested as additives aiming to improve complex formation. Commercial protein transfection reagents Chariot (Ambion) and ProJect (Pierce) were used as positive controls. The transfection efficiency was evaluated using three criteria: the percent of AF488 positive cells, the percent of dead cells (toxicity) and the mean fluorescence intensity (MFI).

Figure 1:
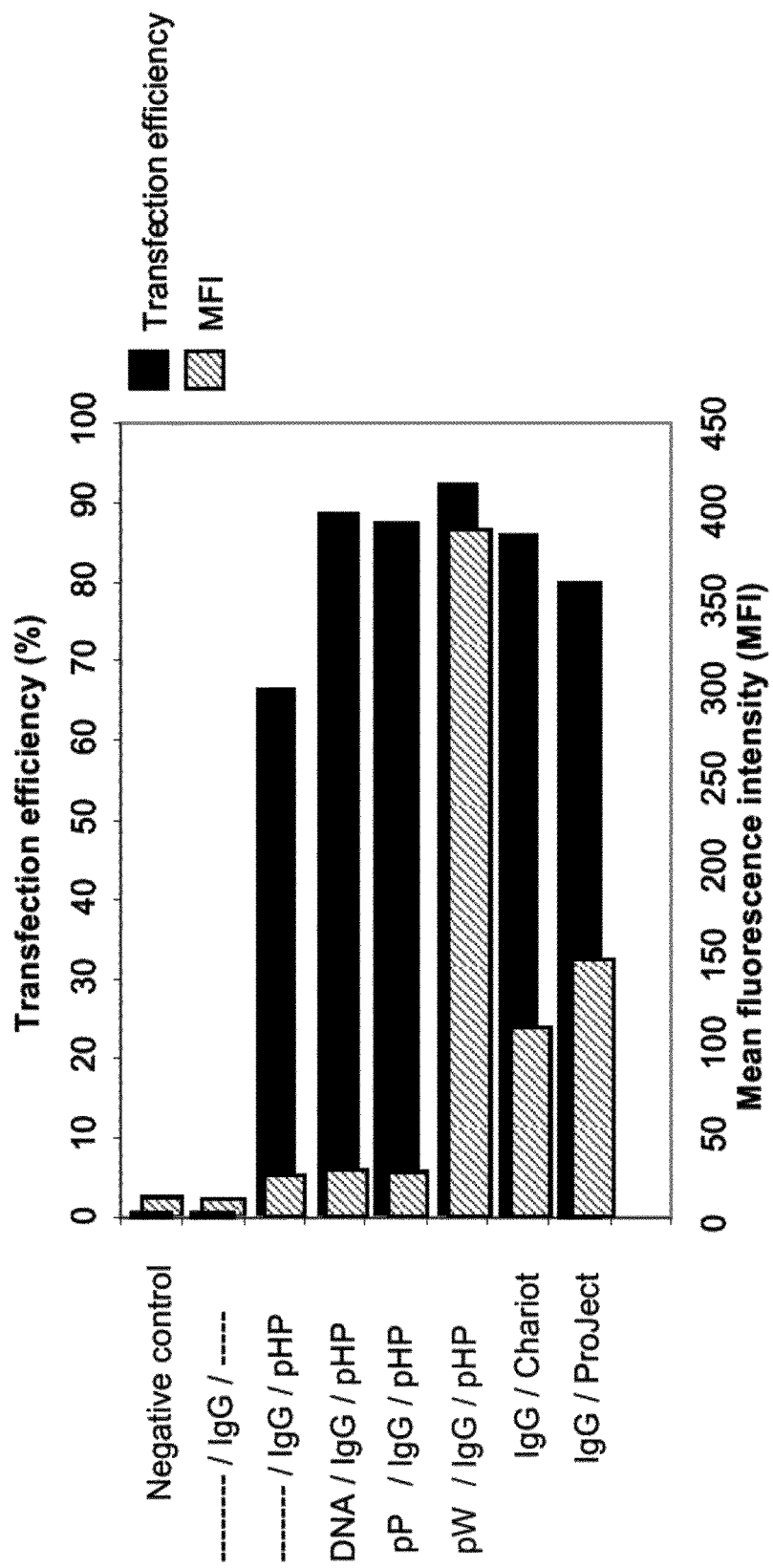
FIG. 1 shows a comparison between embodiments of the invention and the prior art as requested by transfection efficiency and mean fluorescence intensity when delivering labelled antibody to HeLa cells.
Figure 3:
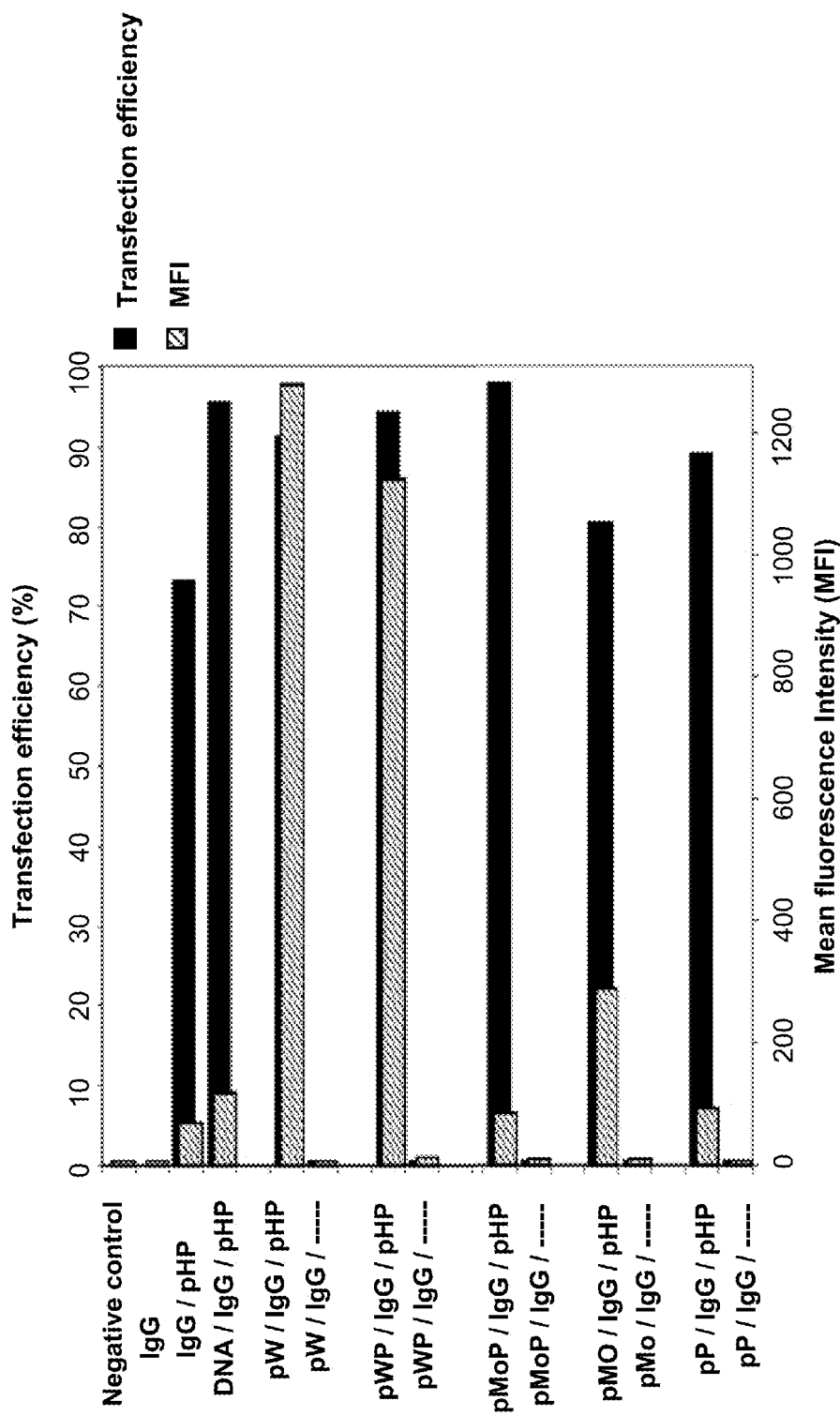
FIG. 3 shows a comparison between different polyanions in relation to the enhancement of cationic polymer mediated protein transfection as measured by transfection efficiency and mean fluorescence intensity.

The results show that antibody cannot internalize into the cell on its own (FIG. 1). The amount of AF488-positive cells increased to 65% when cationic polymer pHP was used in complex with the antibody. The percent of transfected cells was even higher (up to 85-95%) when different polyanions (DNA, pP or pW) were added into the mixture, suggesting that polyanions have positive effect for protein delivery. Polyanions alone, on the other hand, have no effect on protein entry into the cell (FIG. 3). Comparison of obtained antibody transfection results with two commonly used commercial protein transfection reagents—Chariot and Project, reveals very similar transfection efficiencies (85% for Chariot and 80% for Project). However, when comparing the MFI values, the polytungstate evidently is more effective and mediates the biggest amount of protein (MFI ~370) being delivered into the cell, which is significantly higher than that shown for Chariot or ProJect (MFI~100 and 150, respectively).

Figure 2:
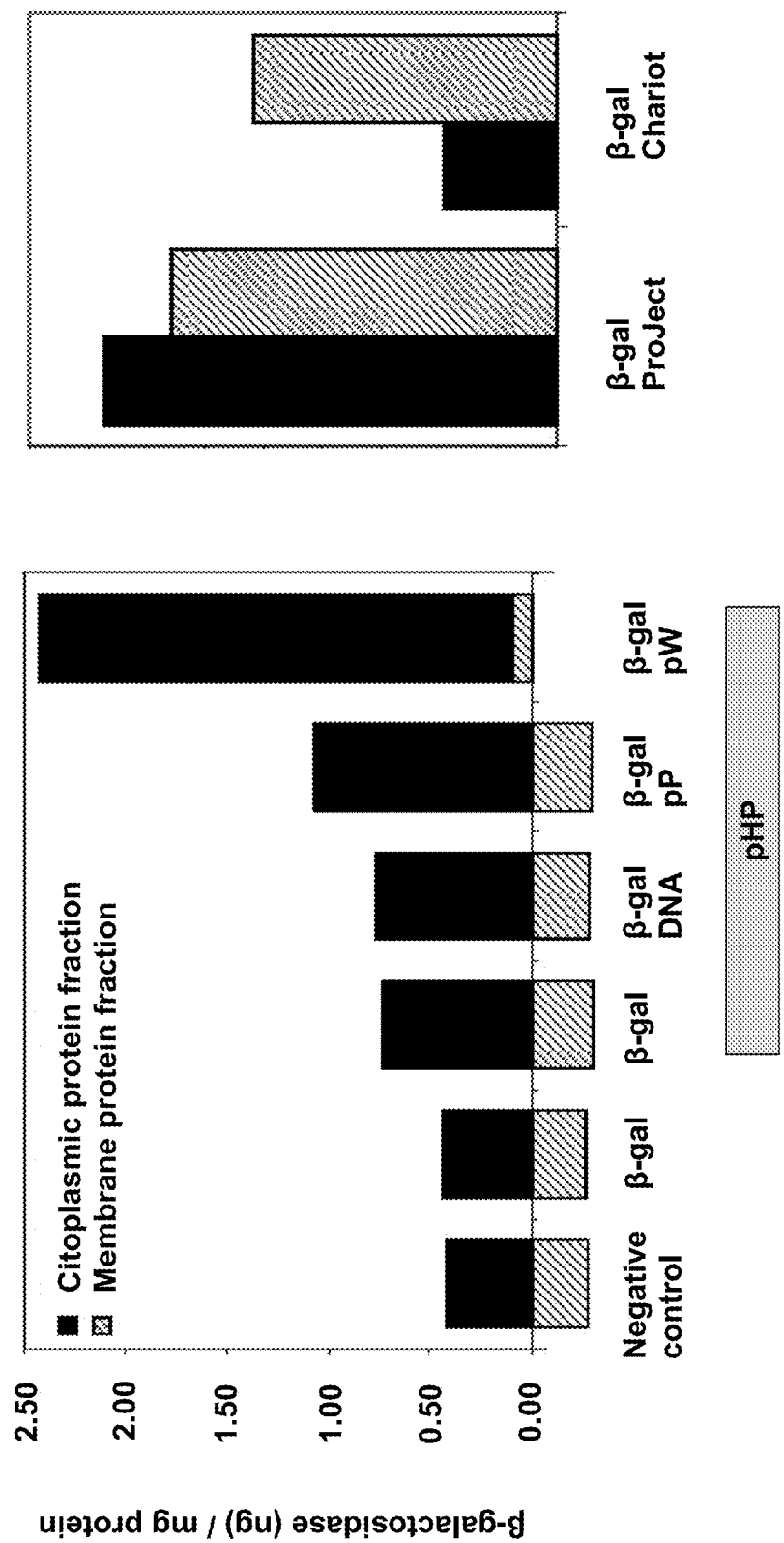
FIG. 2 shows a comparison between embodiments of the invention and the prior art as measured by distribution of transduced β-galactosidase in cytoplasmic and membrane protein fractions.

To determine cellular localization of transduced proteins, the cells were transfected with β-galactosidase using the same compositions and protocols as described above. The cells were further fractionated using ProteoJET™ Membrane Protein Extraction Kit (Fermentas) in order to separate membrane and cytosolic proteins. Enzymatic activity of β-galactosidase was estimated in both fractions (FIG. 2). Results show that majority of β-gal activity was detected in the cytosolic fraction for all pHP and Project-mediated transfections, while very little or no β-gal activity was detected in the membrane fraction of pHP-transfected cells, suggesting that cationic polymer (with or without polyanions) positions transduced proteins exclusively inside the cell. For Project, however, considerable amount of β-gal activity was found in the membrane, indicating that equivalent amount of protein after transfection remains stuck within or on the surface of the cellular membrane. For Chariot-mediated transfection, significantly more β-galactosidase was found in the membrane fraction than in the cytosol. In conclusion, pHP-polyanion mixture facilitates highly efficient protein transduction resulting primarily in cytosolic protein localization inside the cell.

To examine if other polyanions contribute to cationic polymer-mediated protein transduction, we tested sodium phosphomolybdate hydrate (pMoP), ammonium molybdate tetrahydrate (pMo), as well as sodium phosphotungstate tribasic hydrate (pWP) along with previously used polyanions: DNA, pP and pW (FIG. 3). The results show that all analyzed polyanions enhance protein transfection to a similar level of 80-95%. The MFI data, however, singled out polytungstates (with or without hetero atoms) as the most potent enhancers (MFI~1200). The polyoxometalates (POMs) carrying hetero atom (pWP and pMoP) apparently performed slightly worse than POMs without hetero atom (pW and pMo).

Figure 4:
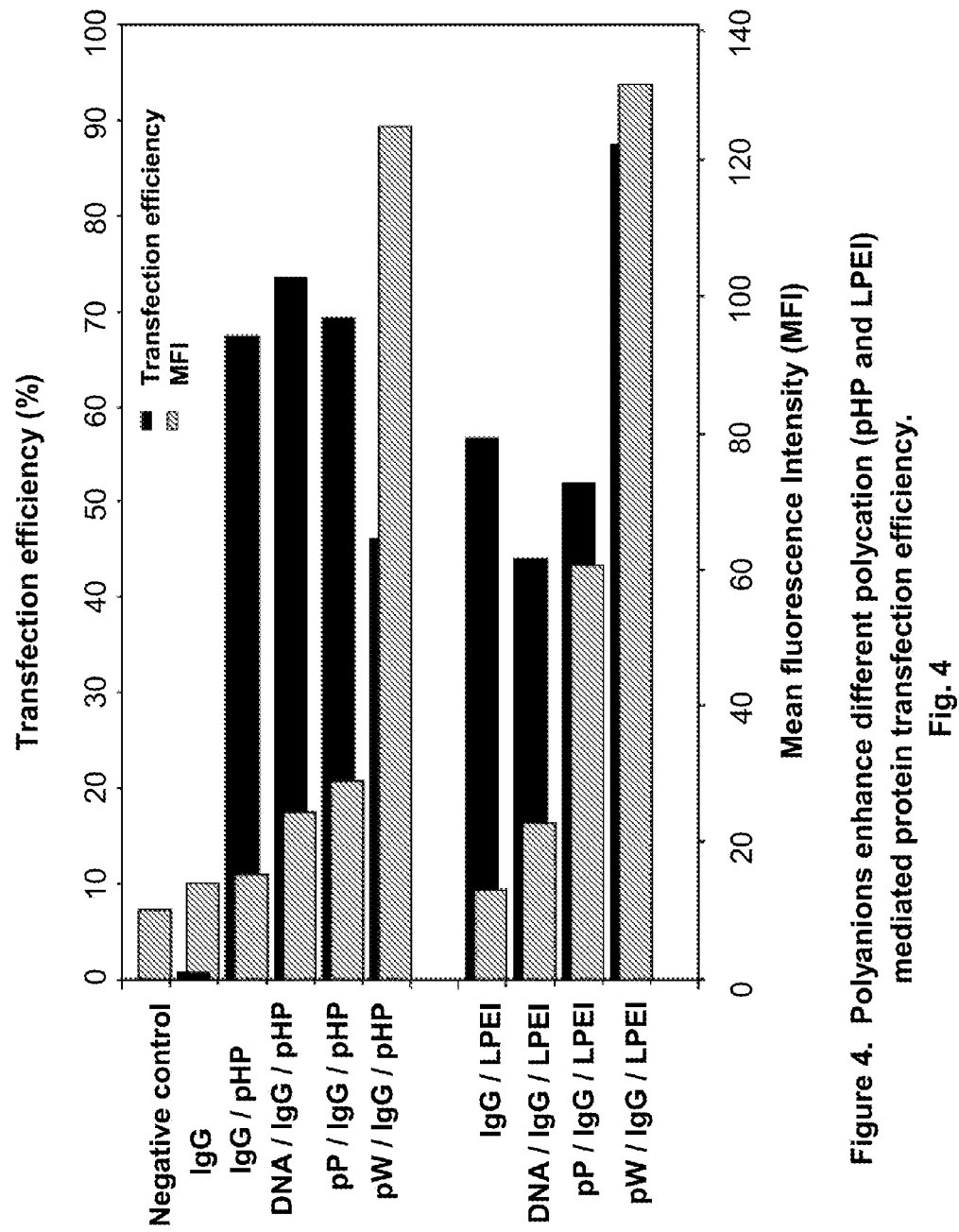
FIG. 4 shows a comparison between different polyanions in the enhancement of protein transfection efficiency by polycations pHP and LPEI, as measured by transfection efficiency and mean fluorescence intensity.

To further investigate if polyanions have positive effect in combination with other polycations used in protein transfections, a popular cationic polymer—LPEI was tested along with pHP in fluorescently labelled antibody transfections. Polyanions—DNA, pP and pW were used to assist protein packaging prior to complexation with LPEI (FIG. 4). The results show that polyanions enhance LPEI-mediated protein transfection as efficiently as pHP-mediated transfection. The MFI values increase from 10 units (protein-LPEI) to 25, 60 and 130 units upon addition of DNA, pP or pW, respectively. The results suggest that negatively charged polyanions may interact with positively charged regions of the antibody and consequently facilitate protein-polyanion interaction with the positively charged polycation.

Figure 5A:
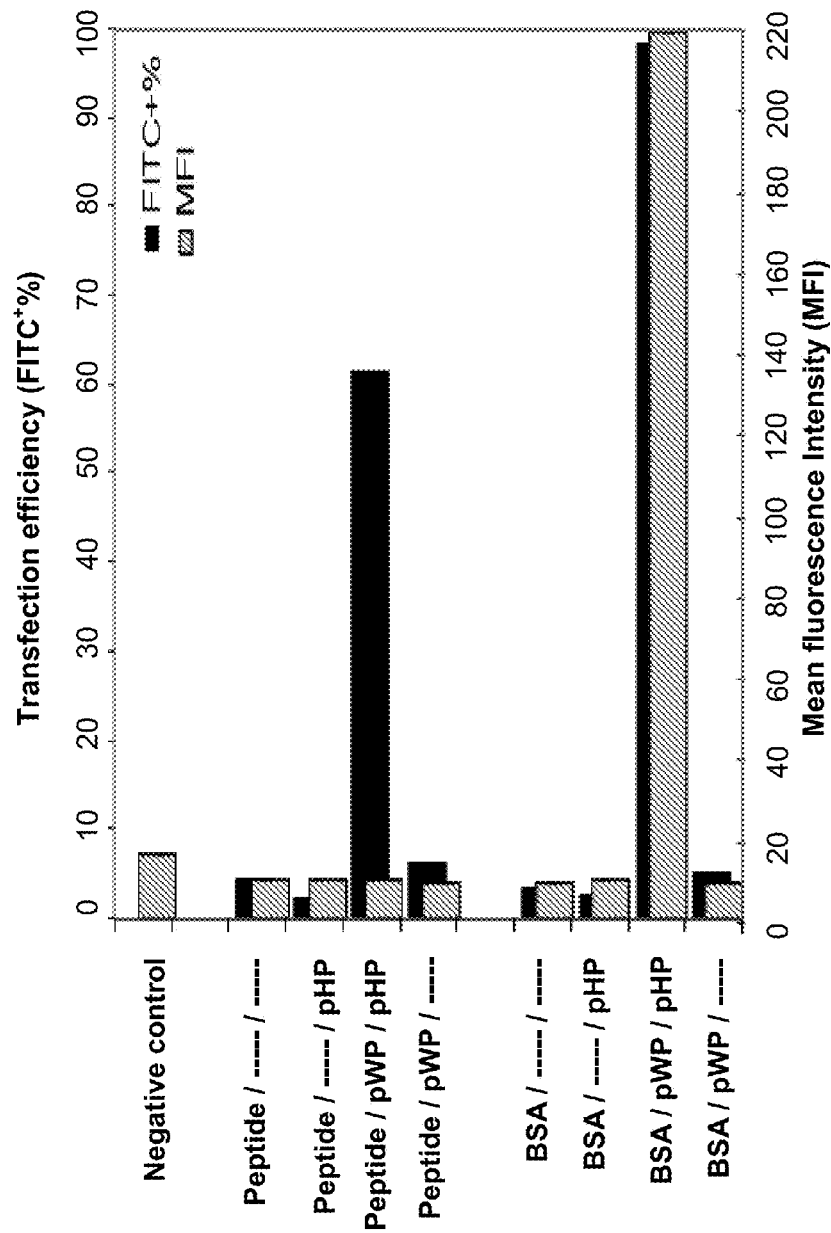
FIG. 5a shows polyanion enhancement of pHP-mediated peptide and inert protein transfection as measured by transfection efficiency and mean fluorescence intensity.
Figure 5B:
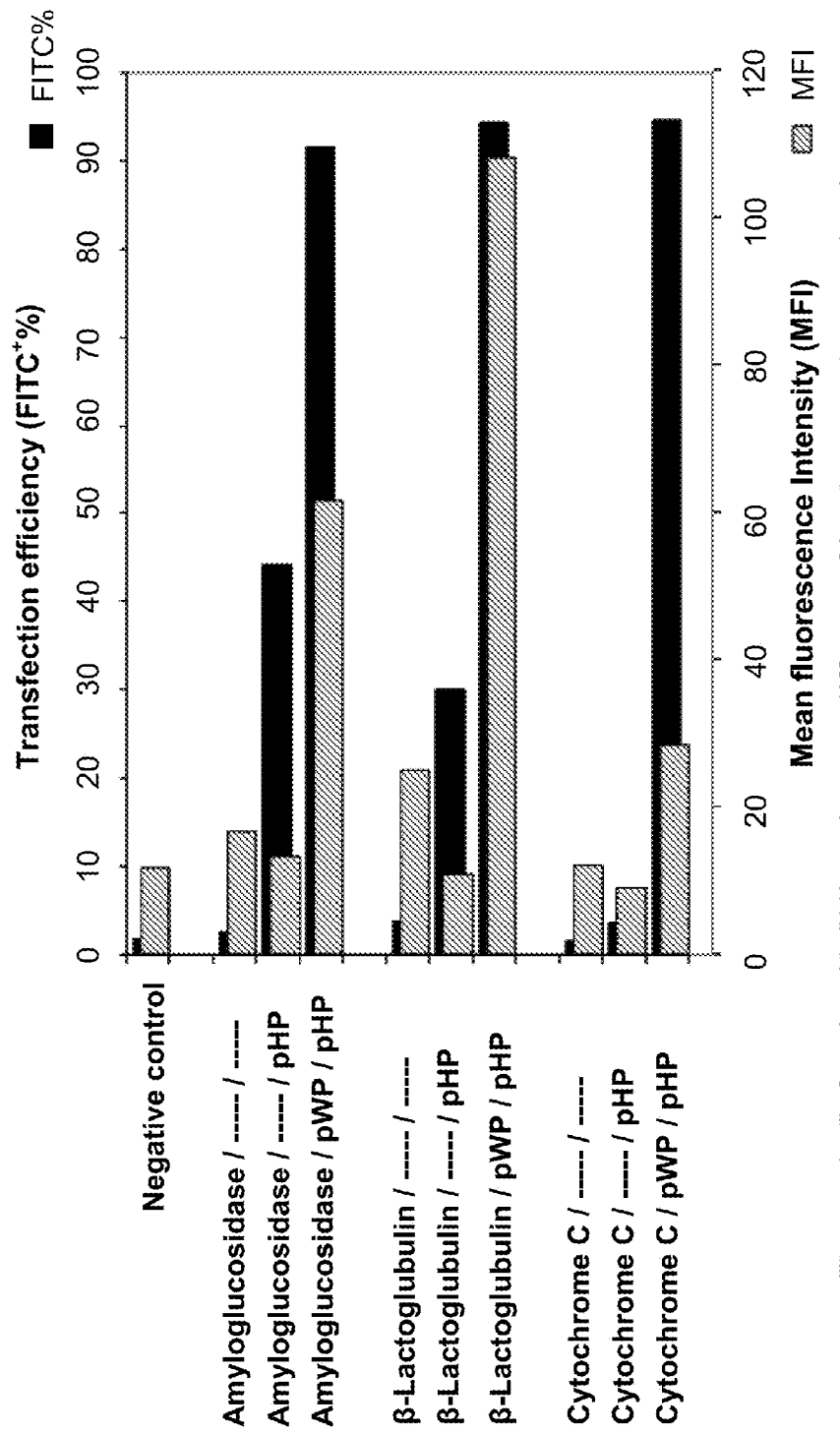
FIG. 5b shows the enhancement of transfection by polyanion PWp of proteins having different pI as measured by transfection efficiency and mean fluorescence intensity.

To demonstrate that polyanions are able to enhance transfection of any type protein, a number of proteins of different size, pI value or function were chemically conjugated to FITC and examined using the same conditions as those used for antibody transfections described above. Successful delivery of 5 kDa peptide (FIG. 5a), 12 kDa cytochrome C, 18 kDa β-lactoglobulin (FIG. 5b), 66 kDa BSA, 97 kDa amyloglucosidase, as well as earlier tested 116 kDa β-galactosidase (FIG. 2) and 150 kDa IgG (FIG. 1, 3, 4), confirm that polyanions enhance transfection of any size protein carried by cationic polymer pHP. The MFI values primarily depend on the size of the protein, i.e. the extent of FITC labelling. Smaller proteins had lower number of FITC molecules and, as a result, their fluorescence was weaker. The transfection of proteins bearing different pI (amyloglucosidase—pI 3.5, β-lactoglobulin pI 5.5, cytochrome C pI 10.5) gave similar results (FIG. 5b), all three proteins were delivered with ~90% efficiency. The amount of polyanion used in this case, depended on the pI of the protein: less polyanion was needed for transfection of amyloglucosidase (0.5 μl), more for transfection of cytochrome C (1.0 μl). Overall, the results show, that polyanion-polycation combination enhances the transfection of proteins with (i) different size, (ii) different pI and (iii) different function.

Figure 6:
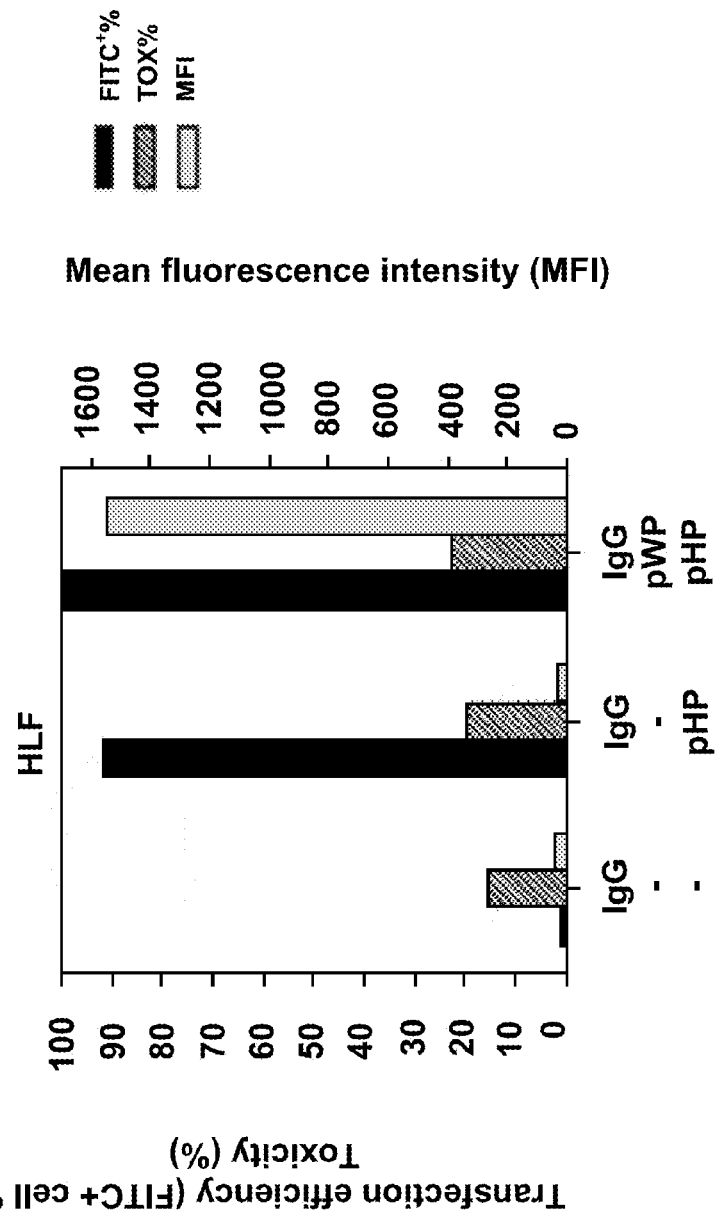
FIG. 6 shows polyanion enhancement of pHP-mediated protein transfection into primary and suspension cells as measured by transfection efficiency, toxicity and mean fluorescence intensity.

For the final evaluation of polyanion exerted effect on the pHP-mediated protein transfection the experiments were carried on different cell types: primary human lung fibroblasts (primary cells—usually difficult to transfect), HeLa S3 (loosely adherent cell line), and Jurkat T cell lymphoma cells (suspension cell line—known to be very difficult to transfect by chemical methods). The results showed that irrespective of the cell type used, the transfection efficiencies reached 90% (FIG. 6). The fluorescence level in strongly adherent HLF cells was the highest (MFI ~1500), while in semiadherent or suspension cells, HeLa S3 and Jurkat, the MFI was 350 and 500, respectively, suggesting that the extent of macromolecule uptake depends on the cell type. Cell size in this experiment should be taken into consideration as well, since HLF cells are significantly bigger, can internalize more material than HeLa S3 or Jurkat cells, and thus fluoresce more intensively than smaller cells. In conclusion, the polyanion (here, pWP) grouping with protein prior to complexation with polycation (pHP) facilitates efficient protein delivery into the primary, adherent and suspension cell types.

Evaluation of polyanion-protein-polycation complex formation after different component mixing schedule and its influence on transfection efficiency was carried out in order to determine the best possible way to form protein-pHP complexes and to ensure the most efficient cargo transport through the cellular membrane. The results apparently were very similar, no matter how the components were mixed together (FIG. 7), the transfection efficiencies ranged from 80 to 95%. Slightly lower MFI values (200 units) suggested that protein should not be the last element added into the mix, but rather mixed with either polycation or polyanion first.

Example 1

Analysis of the Protein Transfection Using pHP

Transfection of HeLa (Human cervical carcinoma-derived cell line) cells was carried out as follows: one day before the transfection experiment, the cells were seeded in a 24-well tissue culture plate at the density of $5 \times 10^4$ cells per well in the total volume of 1 ml DMEM culture medium supplemented with 10% FBS. The cells were incubated at 37° C. in a $CO_2$ incubator until they reached 70-80% confluency (usually within 24 h). On the day of transfection, the growth medium was removed and replaced with 0.5 ml of warm serum-free medium. Alexa Fluor 488-labeled goat IgG antibody (1 μg) was diluted in 100 μl of 0.15M NaCl solution and mixed with different amounts of polyanions: DNA (1 μg pUC18), sodium polyphosphate (10 mM pP—1 μl) or sodium polytungstate (10 Mm pW—3 μl). Cationic polymer pHP (1 μl) was added into the protein-polyanion mixture and vortexed immediately for few seconds to ensure even distribution of the material. The complexes were allowed to form for 15-20 min at room temperature and added to the cell culture in a drop-wise manner. The cells were further incubated for 2 h at 37° C. in a $CO_2$ incubator. To remove unincorporated complexes, the cultures were rinsed with PBS, and the cells were analyzed by FACS (Fluorescence Activated Cell Sorter). Transfections using Chariot (Ambion) and ProJect (Pierce) reagents were carried out following manufacturer suggested protocols.

Example 2

Analysis of the Protein Localization after Polyanion-Polycation Mediated Transfection HeLa cell transfection with β-galactosidase (1 μg) was carried out using the same protocol and conditions as described above. The cells were further fractionated using ProteoJET™ Membrane Protein Extraction Kit (Fermentas) in order to separate membrane and cytoplasmic proteins. The enzymatic activity of β-galactosidase in both fractions was estimated using colorimetric assay.

Example 3

Analysis of Different Polyanions in pHP-Mediated Protein Transfections

Several different polyanions were tested for their ability to improve labelled-IgG transfection. Polyanions were grouped as follows: (i) phosphates—heterophosphates (DNA) and homophates (sodium polyphosphate—pP), (ii) POMs—without hetero atom (sodium polytungstate, pW, or ammonium molybdate tetrahydrate, pMo) and with hetero atom (sodium phosphotungstate tribasic hydrate, pWP, and sodium phosphomolybdate hydrate, pMoP). HeLa cells were prepared for transfection essentially as described in Example 1. The amount of each polyanion used was: 3 μl of pW, pWP or pMoP, and 2 μl of pMo (each 10 mM stock concentration), 0.5 μl of pP (30 mM stock concentration), 1 μg of DNA. Polyanion-Antibody-pHP mixtures were incubated for 15 min and added to the cells in a drop-wise manner. Transfection results were processed 2 h later using Guava Easy Cyte Plus flow cytometry system (Millipore).

Example 4

Analysis of Polyanions in Different Polycation-Mediated Protein Transfection

Cationic polymer LPEI (ExGen 500) was tested in Alexa Fluor 488-labeled goat IgG transfection using polyanions—DNA, pP and pW to assist the protein packaging prior to complexation with LPEI. Chinese hamster ovary cells (CHOk1) were prepared for transfection essentially the same way as HeLa cells (example 1). The cells were cultured in RPMI medium supplemented with 10% FBS, the transfection was carried out in serum free RPMI medium. The complexes were formed the same way as described in example 1 for pHP, the amount of LPEI used—3.3 μl.

Example 5

Analysis of Polyanions in Transfections of Proteins of Different Size and pI

FITC-labeled proteins—5 kDa peptide, BSA, amyloglucosidase (pI 3.5), β-lactoglobulin (pI 5.5) and cytochrome-C (pI 10.5) were transfected into HeLa cells following the procedure described in Example 1. The amount of pWP used: 0.5 μl for amyloglucosidase and β-lactoglobulin, 1 μl for cytochrome C.

Example 6

Analysis of the Polyanion Effect on Difficult to Transfect Cell Lines

Comparison of protein transfer efficiency using pHP and polyanions (pWP) was tested in suspension cell lines, HeLa S3 and Jurkat (Human T cell lymphoma cell line), as well as in primary cells HLF (human lung fibroblasts). Suspension cells were seeded at the density of $2 \times 10^5$ cells/well, HLF $5 \times 10^4$/well 24 hours before the transfection. Antibody-pHP complexes in 0.15 M NaCl solution were prepared as described earlier.

Example 7

Analysis of the Component Mixing Order Effect on Protein Transfection

HeLa cells were prepared for transfection as described in Example 1. The antibody IgG (1 μg)—pWP (1 μl)—pHP (1 μl) complexes were prepared in 0.15 M NaCl following different component mixing order: IgG+PA+pHP, PA+IgG+pHP, IgG+pHP+PA, pHP+IgG+PA PA+pHP+IgG, and pHP+PA+IgG. Complexes were allowed to form for 15 min and added to the cells in a drop-wise manner.

The invention claimed is:

1. A composition for delivering a peptide or protein into a cell, which composition comprises a polycationic agent and a polyanionic agent, wherein the polyanionic agent is a nucleic acid and the polycationic agent is a modified polyalkyleneimine polymer having a repeat unit of formula I or formula V:

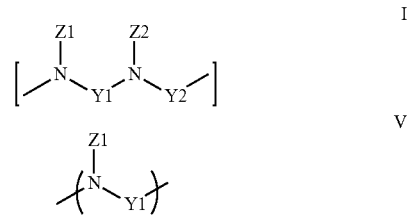

where:
Z1 and Z2 each independently represent —H, alkyl or a branching chain;
Y1 and Y2 each independently represent a group having formula II or III:

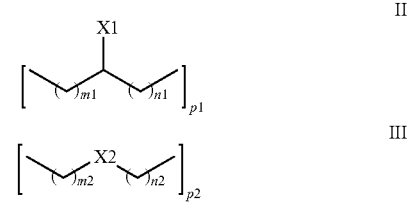

where:
X1 is selected from the group consisting of —H, -alkyl, —SH, —CN, —NH$_2$, —N(alkyl)$_2$,—NH(alkyl), —CONH$_2$-,

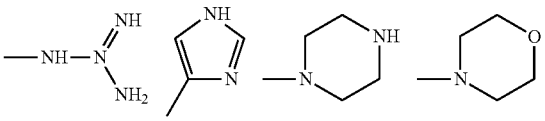

—NHCONH$_2$,
X2 is selected from the group consisting of —CH$_2$—, —O—, —S—, —NH—, or —N(alkyl)-;
provided that at least one of X1 and X2 is a hydrophilic group;
m1, m2, n1 and n2 each independently is 0, 1, 2 or 3; and
p1 and p2 each independently is 1 or 2.

2. The composition of claim 1, wherein the nucleic acid is DNA.

3. A kit for delivering a peptide or protein into a cell, which kit comprises a polycationic agent in a first container and a polyanionic agent in a second container, wherein the polyanionic agent is a nucleic acid and the polycationic agent is a modified polyalkyleneimine polymer having a repeat unit of formula I or formula V:

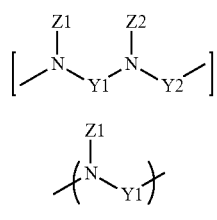

I

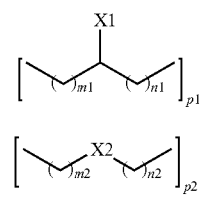

V where:
Z1 and Z2 each independently represent —H, alkyl or a branching chain;
Y1 and Y2 each independently represent a group having formula II or III:

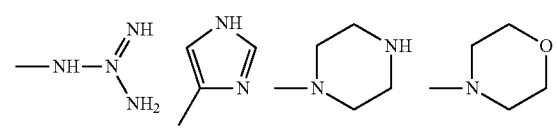

where:
X1 is selected from the group consisting of —H, -alkyl, —SH, —CN, —NH₂, —N(alkyl)₂, —NH(alkyl), —CONH₂-, CONH₂, —NHCONH₂,
X2 is selected from the group consisting of —CH₂—, —O—, —S—, —NH—, or —N(alkyl)-;
provided that at least one of X1 and X2 is a hydrophilic group;
m1, m2, n1 and n2 each independently is 0, 1, 2 or 3; and
p1 and p2 each independently is 1 or 2.

4. The kit of claim 3 where the nucleic acid is DNA.

5. A method for delivering a peptide or protein into a target cell, which method comprises contacting the peptide or protein with a polycationic agent and a polyanionic agent to form a complex and contacting the complex with the target cell so as to deliver the peptide or protein thereto, wherein:
(1) the polyanionic agent is a nucleic acid; and
(2) the polycationic agent is a modified polyalkyleneimine polymer having a repeat unit of formula I or formula V:

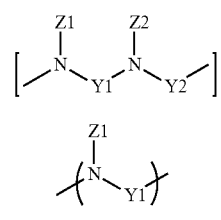

I

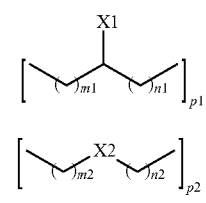

V where:
Z1 and Z2 each independently represent —H, alkyl or a branching chain;
Y1 and Y2 each independently represent a group having formula II or III:

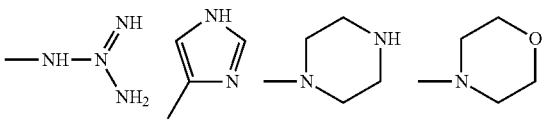

where:
X1 is selected from the group consisting of —H, -alkyl, —SH, —CN, —NH₂, —N(alkyl)₂, —NH(alkyl), —CONH₂, —NHCONH₂,
X2 is selected from the group consisting of —CH₂—, —O—, —S—, —NH—, or —N(alkyl)-;
provided that at least one of X1 and X2 is a hydrophilic group;
m1, m2, n1 and n2 each independently is 0, 1, 2 or 3; and
p1 and p2 each independently is 1 or 2.

6. The method according to claim 5, wherein the peptide or protein is contacted with the polyanionic agent prior to contacting the polycationic agent.

7. The method according to claim 5, wherein the peptide or protein comprises an enzyme, an antibody or an inert protein.

8. The method according to claim 5, wherein the target cell is a suspension cell, an adherent cell, a primary cell or cultured cell.

9. The method of claim 5 where the nucleic acid is DNA.

* * * * *

UNITED STATES PATENT AND TRADEMARK OFFICE
CERTIFICATE OF CORRECTION

PATENT NO.        : 9,856,456 B2
APPLICATION NO.   : 14/863539
DATED             : January 30, 2018
INVENTOR(S)       : Lagunavicius It is certified that error appears in the above-identified patent and that said Letters Patent is hereby corrected as shown below:

In the Claims

In Claim 1, at Column 16, Line 43 reads:
"—CONH2-,"
It should read:
-- —CONH2, --

In Claim 1, at Column 16, Line 57 reads:
"m1, m2, n1 and n2 each independently is 0, 1, 2or 3; and"
It should read:
-- m1, m2, n1 and n3 each independently is 0, 1, 2 or 3; and --

In Claim 3, at Column 17, Line 13 reads:
"Z1and Z2"
It should read:
-- Z1 and Z2 --

In Claim 3, at Column 17, Line 31 reads:
"—CONH2-,"
It should read:
-- —CONH2, --

In Claim 3, at Column 17, Line 40 reads:
"—CONH2, —NHCONH2,"
It should read:
-- —NHCONH2, --

Signed and Sealed this
Twentieth Day of March, 2018

Andrei Iancu
*Director of the United States Patent and Trademark Office*

CERTIFICATE OF CORRECTION (continued)
U.S. Pat. No. 9,856,456 B2

In Claim 3, at Column 17, Line 41 reads:
"X2is selected"
It should read:
-- X2 is selected --

In Claim 3, at Column 17, Line 45 reads:
"m1, m2, n1 and n2 each independently is 0, 1, 2or 3; and"
It should read:
-- m1, m2, n1 and n2 each independently is 0, 1, 2 or 3; and --